United States Patent [19]

Jackson

[11] Patent Number: 5,087,420
[45] Date of Patent: Feb. 11, 1992

[54] APPARATUS FOR TREATMENT AND DISPOSAL OF INFECTIOUS WASTE

[75] Inventor: Edward E. Jackson, Knightstown, Ind.

[73] Assignee: Puretech Systems, Inc., Indianapolis, Ind.

[21] Appl. No.: 258,156

[22] Filed: Oct. 14, 1988

[51] Int. Cl.$^5$ ................................. A61L 2/18
[52] U.S. Cl. ..................... 422/37; 210/173; 210/765; 241/21; 241/22; 241/101.8; 241/38; 366/137; 366/153; 422/28; 422/184; 422/261; 422/286
[58] Field of Search ................... 241/21-22, 241/46.06, 101 B, 33, 38; 422/184, 37, 261, 28, 286; 366/136-137, 153; 210/764, 194, 754, 765, 173, 138, 97, 195.1

[56] References Cited

U.S. PATENT DOCUMENTS

| | | | |
|---|---|---|---|
| 2,520,320 | 8/1950 | Lyons et al. | 241/33 X |
| 2,609,331 | 9/1952 | Cheney | 241/21 X |
| 2,676,666 | 4/1954 | Howe | 210/173 |
| 2,737,129 | 3/1956 | Johnson et al. | 241/38 X |
| 2,880,941 | 4/1959 | Fox et al. | 241/38 X |
| 3,563,384 | 2/1971 | DeLaney | 210/152 |
| 3,567,633 | 3/1971 | Valdespino | 210/173 X |
| 3,688,993 | 9/1972 | Church | 241/38 X |
| 3,699,592 | 10/1972 | Minchack | 210/173 X |
| 3,824,632 | 7/1974 | Bach et al. | 210/173 X |
| 3,965,006 | 6/1976 | Ohe, Jr. | 210/138 |
| 4,023,735 | 5/1977 | Schnell | 241/22 |
| 4,032,446 | 6/1977 | Miller, Jr. | 210/152 |
| 4,185,973 | 1/1980 | Tester | 241/33 X |
| 4,233,157 | 11/1980 | Miller | 210/137 |
| 4,378,093 | 3/1983 | Keener | 241/46.06 X |
| 4,471,916 | 9/1984 | Donaldson | 241/101 B |

*Primary Examiner*—Robert J. Warden
*Assistant Examiner*—Amalia L. Santiago
*Attorney, Agent, or Firm*—Woodard, Emhardt, Naughton, Moriarty & McNett

[57] ABSTRACT

An improved infectious waste treatment system wherein infectious waste is fragmented and converted to a liquid or liquid/sludge form and then is chemically disinfected in a precisely controlled and timed batch process. The disinfection process takes place in an airtight sealed container to insure against release of pathogenic agents into the atmosphere. The process produces a non-toxic and non-infectious liquid or liquid/sludge waste residue which can be safely released into a sanitary sewer, landfilled or otherwise environmentally disposed.

21 Claims, 4 Drawing Sheets

APPARATUS FOR TREATMENT AND DISPOSAL OF INFECTIOUS WASTE

BACKGROUND OF THE INVENTION

The present invention relates generally to waste treatment and, in particular, to a waste disposal system for treating and disposing of infectious or biohazardous waste in a manner whereby the waste is chemically treated in a precisely controlled batch process so as to produce a non-toxic and non-infectious liquid or liquid/sludge residue that can be safely discharged into a sanitary sewer or landfill.

In recent years, the category of "infectious waste" has become more clearly defined as a category of environmental waste material having treatment and disposal requirements which are distinctly different from other types of non-hazardous and hazardous wastes. There has been a developing understanding that pathogenic agents which are the focus of infectious waste are transmitted primarily by blood, blood products, body fluids, bone, and tissue, and secondarily by the containers, gloves, syringes, diapers, dressings, and other objects which have come in contact with the above mentioned biological products.

Effective treatment of infectious waste requires a treatment system which is effective against bacteria and viruses as well as other potentially pathogenic agents. Proper treatment of all of these forms of infectious waste requires a precisely controlled process whereby all pathogenic agents contained in the infectious waste come in contact with a chemical of sufficient content and concentration for a sufficient length of contact time to neutralize these pathogenic agents. Ideally, such a process should have the capability to be easily adjusted according to the volume and type of infectious waste being treated.

Waste treatment processes have been developed which either address certain specific types of biological or non-biological waste materials or all forms of waste generated by a particular type of generator, such as a hospital. However, such waste disposal processes have not focused exclusively on infectious waste. Therefore, such processes and systems are either not economically practicable or are otherwise unsuitable for many infectious waste generators.

In recent years waste treatment processes have been developed to provide some level of treatment of infectious waste. However, such treatment has either focused on the neutralization of bacteria only or lacked the control necessary to insure that all potentially pathogenic agents present in infectious waste, as described above, are effectively treated.

SUMMARY OF THE INVENTION

The present invention provides an apparatus and method for infectious waste treatment whereby blood and other biological products, as well as disposable objects which have come in contact with such products, are first reduced to a liquid or liquid/sludge state and then treated in a batch process in which the volume of infectious waste, the formula and concentration of the chemical, and the time of contact of the chemical with the waste are precisely controlled so as to render the infectious waste non-toxic and non-infectious, thus allowing for safe disposal of the treated liquid or liquid/sludge residue in a sanitary sewer, landfill or other disposal source.

The invention can be used as a point source treatment process, whereby infectious waste can be treated and rendered non-toxic and non-infectious on-site, eliminating the need for any further handling or treatment.

It is an object of the present invention to treat and render non-toxic and non-infectious all bacterial, viral, and other pathogenic agents potentially found in infectious waste that includes blood, blood products, body fluids, bone, tissue, and other biological material, and disposables such as containers, gloves, syringes, diapers, dressings, and other objects that have come in contact with blood and other biological products.

Another object of the present invention is to treat the above described infectious waste in a batch process, rather than a continuous process, allowing for the precise treatment of a measured volume of infectious waste at a time.

Another object of the present invention is to treat the above described infectious waste using a disinfectant chemical, preferably in a solid tablet form, which is broken down and dissolved in a liquid in the same manner as the infectious waste being processed.

Another object of the present invention is to break down the above described infectious waste in a maceration or grinder pump process which converts the infectious waste in to a liquid or liquid sludge with the biological component having a particle size of not greater than 1/16th of an inch. The reduction in size and conversion of the infectious waste to a liquid or liquid sludge state, insures that the chemical comes in contact for an adequate time with every pathogenic agent contained in the infectious waste being treated.

Another object of the present invention is to treat the above described infectious waste in a reservoir/pump process which recirculates the liquid or liquid sludge and the chemical, through the pump and reservoir for a detention time sufficient for contact of the infectious waste with the chemical to render non-toxic and non-infectious the type of infectious waste being treated.

Another object of the present invention is to treat the above described infectious waste to a degree sufficient to allow for the safe disposal of the liquid or liquid sludge residue in a sanitary sewer and/or landfill.

Another object of the present invention is to allow for the controlled batch testing of the liquid or liquid sludge residue, remaining after treatment, for such characteristics as biological composition (biological oxygen demand, chemical oxygen demand, etc.), chemical composition, and presence of pathogenic agents.

These and other objects of the present invention will become more apparent by reference to the detailed specification, claims, and drawings.

DESCRIPTION OF THE PREFERRED EMBODIMENT

Figure 1:
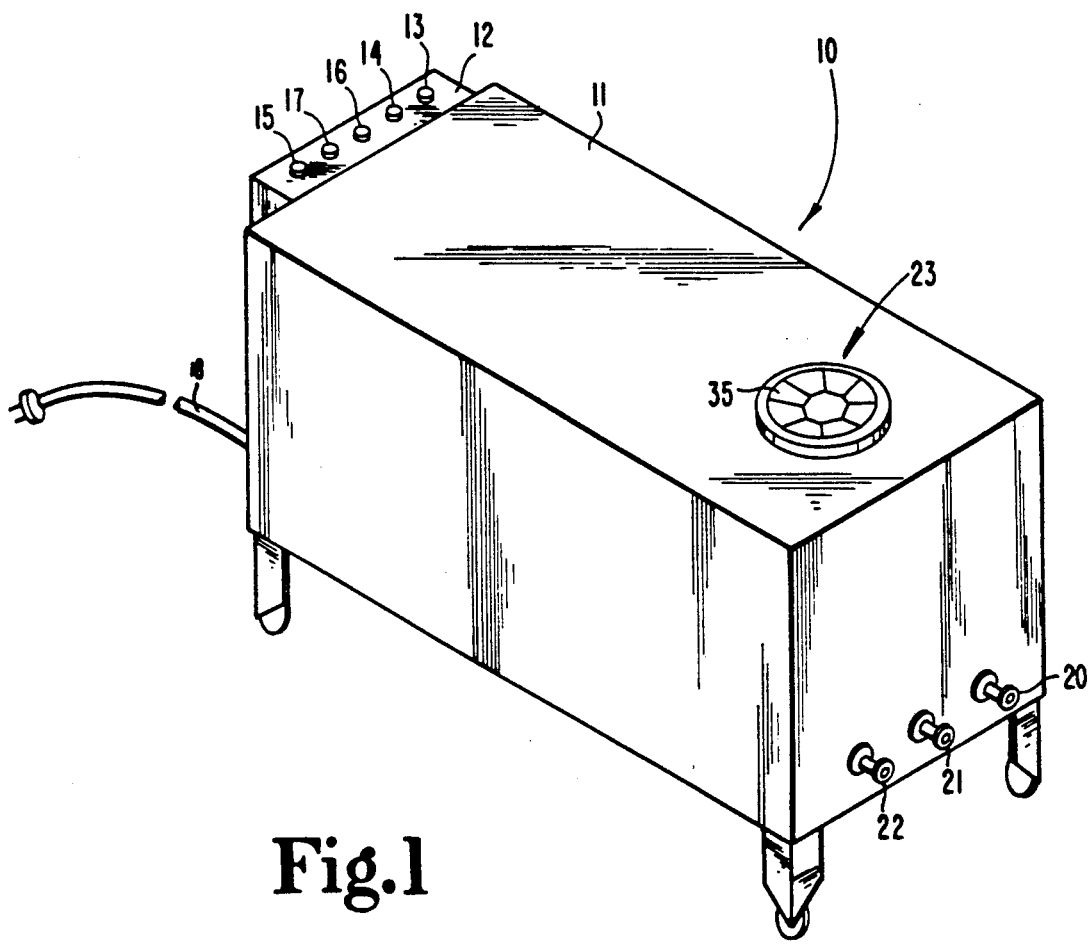
FIG. 1 is a perspective view of the infectious waste treatment apparatus of the present invention.
Figure 2:
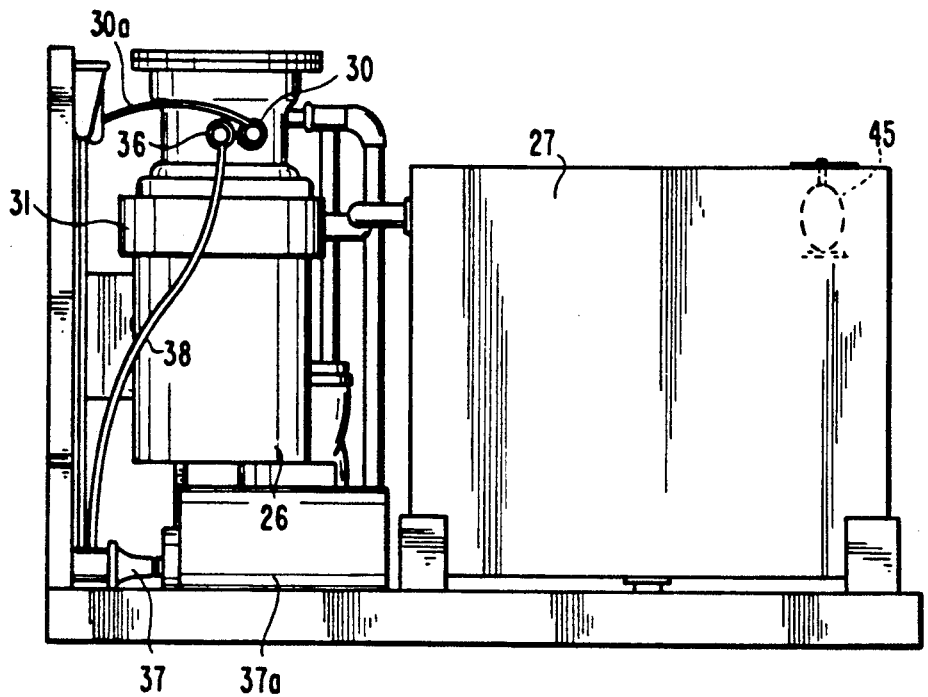
FIG. 2 is a right side elevation view of the apparatus of FIG. 1 with the outer housing removed.
Figure 3:
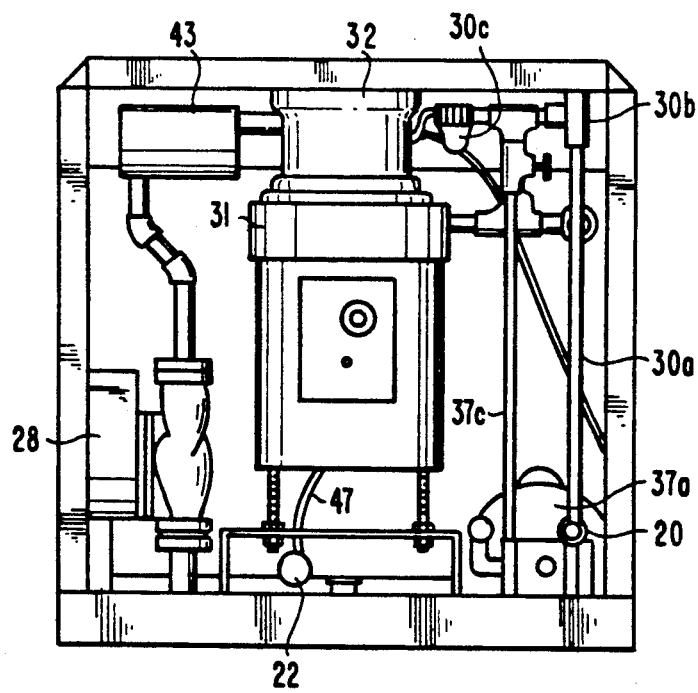
FIG. 3 is a front elevation view of the apparatus of FIG. 1 with the outer housing removed.
Figure 4:
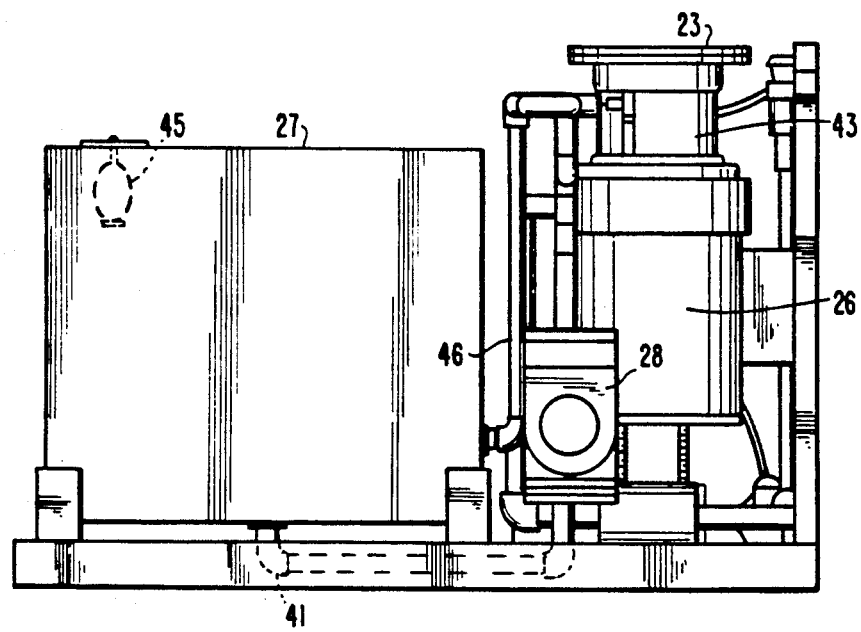
FIG. 4 is a left side elevation view of the apparatus of FIG. 1 with the outer housing removed.
Figure 5:
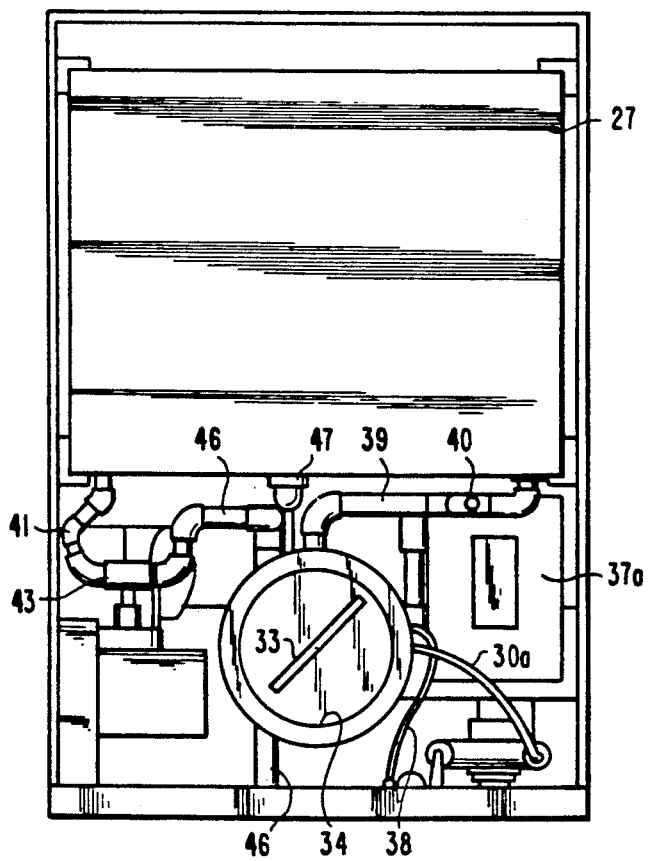
FIG. 5 is a top view of the apparatus of FIG. 1 with the outer housing removed.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to the drawings, FIG. 1 shows the apparatus of the invention generally designated at 10. All of the components of the apparatus 10 are enclosed in an exterior housing 11 made of non-corrosive materials such as stainless steel to facilitate cleaning.

At one end of the housing 11 is an electronic control panel 12 which provides all of the major operator controls for the apparatus 10. On the exterior of the control panel 12 is a power on switch 13, a power off/reset switch 14, a waste discharge indicator light 15, a processor forward/off/reverse switch 16, and an aspirator on/off switch 17. Connection to a suitable source of electric power to power the apparatus 10 is provided by electric power cord 18.

A the opposite end of the housing 11 from the control panel 12 is a water line inlet 20, an aspirator inlet 21, and a waste discharge line outlet 22. Infectious waste material may be received into the apparatus 10 through an inlet 23 located at the top of the housing 11 or, alternatively if desired, through a conventional aspirator suction line 24 (shown schematically in FIG. 6) which may be coupled to aspirator inlet 21.

Referring to FIGS. 2-5, the various inner components of the apparatus 10 are shown. Generally, the major components include a macerator 26 which comminuted the waste material received from aspirator suction time 24 or through waste inlet 23, a reservoir 27 which receives the comminuted waste material from macerator 26 for batch treatment, and a recirculation/discharge pump 28 for mixing the comminuted waste material in reservoir 27 with a chemical disinfectant and discharging the treated waste material from the reservoir.

Waste inlet 23 opens upwardly from the top of macerator 26 and communicates with macerating chamber 31 through a channel 32 comprising the throat of the macerator. Inside channel 32 is a water inlet 30 which communicates through supply line 30a with water line inlet 20. A one way valve 30b prevents backflow of liquid from macerating chamber 31 into line 30a while on/off valve 30c controls the flow of water into macerating chamber 31, thereby permitting water from a suitable external source (not shown) to be flushed into the macerating chamber 31 during operation.

A pump 37 and motor 37a provides a source of vacuum for aspiration through aspirator line 37b which communicates with aspirator inlet 21. Aspirated waste from line 37b along with water from line 37c is pumped through pump 37 to line 38 which communicates to an inlet opening 36 separate from inlet 30 inside channel 32.

The macerator 26 includes a rotating cutter bar 33 and grooved shredder ring 34 which cooperate to comminute the waste material by a shredding or cutting action as the waste material is thrown to the peripheral sides of the macerating chamber by centrifugal force. A splash guard 35 made of rubber or a suitable flexible plastic material is mounted within waste inlet 23 to prevent waste material, chemical disinfectant, or water from splashing out of the inlet 23 during operation.

In order to effectively treat the infectious waste material, the macerator 26 must be capable of fragmenting the biological component of the waste material to a particulate size no larger than 1/16" diameter. In the preferred embodiment macerator 26 is a commercially known design used to process food waste such as in the food service industry, and is available from In-sink-erator Division of Emerson Electric Co. under model no. SS75. Alternatively, macerator 26 may be replaced by a grinder pump which comminutes the waste material by a grinding action as opposed to a cutting action.

The reservoir 27 is fully enclosed and all openings in reservoir 27 which communicate externally of the apparatus 10 are valve sealed to render the reservoir airtight, thereby preventing the escape of airborne or waterborne contaminants during the treatment process.

A conduit 39 communicates between macerating chamber 31 and the upper portion of reservoir 27 to convey the comminuted waste material to reservoir 27. Check valve 40 in conduit 39 prevents backflow into macerator 26. Inside of the reservoir 27 is a float-type level indicator 45. A waste discharge/recirculation line 41 extends from the bottom of reservoir 27 and communicates with pump 28 which is an open face impeller type pump. The discharge end of pump 28 communicates with a 3-way valve 43 which routes the discharge from pump 28 either to a return line 44 communicating with reservoir 27 or to a waste discharge line 46 communicating with waste discharge line outlet 22.

In order to keep the solids component of the waste material in suspension in reservoir 27 and thereby optimize contact time with the disinfectant chemical, the return line 44 is located near the bottom of reservoir 27. From this location, the discharge through the return line 44 serves to flush the bottom of the reservoir 27, enhancing the mixing effect.

Also connected to the discharge line 46 is an air vent line 47 which communicates with the upper portion of reservoir 27 to provide ventilation thereof while preventing escape of airborne contaminants to the ambient air.

WASTE SYSTEM OPERATIONAL DESCRIPTION

Figure 6:
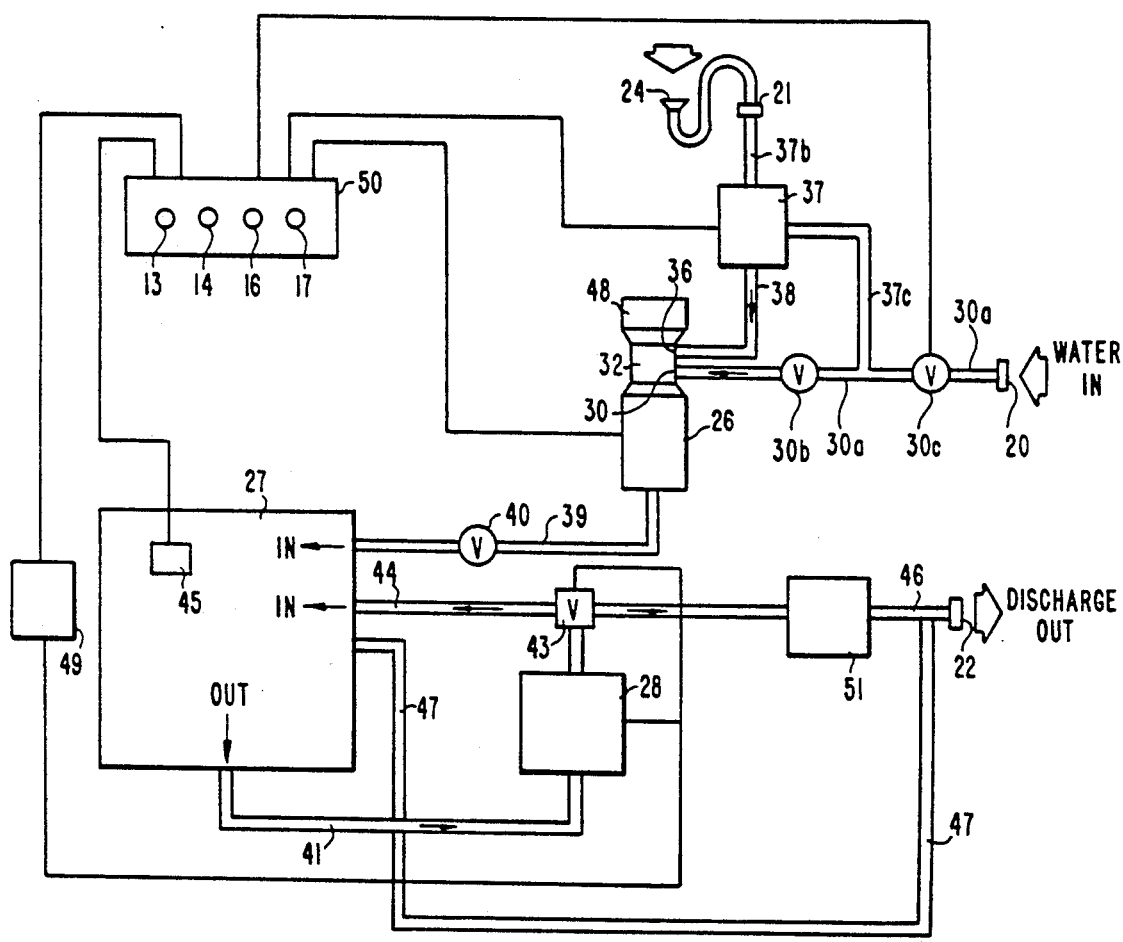
FIG. 6 is a block diagram schematic illustrating the processing and control system of the present invention.

Referring now also to FIG. 6, the operation and control of the apparatus will now be described in detail. In order to ready the apparatus 10 for operation, power cord 18 is connected to an exterior electrical power source, water line inlet 20 is connected to a suitable water supply, aspirator inlet 21 is connected to an aspirator suction line 24, and the discharge line outlet 22 is coupled to a suitable disposal source, such as for example a sanitary sewer system.

To begin operation of the apparatus 10, the power on switch 13 is activated to the "on" position. In the "on" position, power is directed to the waste processor forward/off/reverse switch 16, the power off/reset switch 14 and the level indicator 45 located in the reservoir 27.

To begin processing waste material, the waste processor forward/off/reverse switch 16 is turned to the forward or reverse position. When the switch 16 is turned to the forward or reverse position, the motor inside the macerator 26 is activated, which in turn activates the rotating cutter bar in the macerator. At the same time, switch 16 activates the on/off valve 30c for water line 16 to its "on" or open position. Water flows from the water line inlet 20 through supply line 30a, and into macerator 26 through inlet 30. Waste material fed into the waste inlet 23 proceeds by gravity to the macerating chamber 31.

When the forward/off/reverse switch 16 is in the forward or reverse position, power is directed to the aspirator on/off switch 17. When the aspirator on/off switch 17 is in the "on" position, the motor 37a to the aspirator pump 37 is activated and water flows from water line 20 through the aspirator pump 37. At the same time the aspirator pump 37 draws waste and air into the aspirator inlet 21, through the aspirator pump 37 and aspirator line 38 into channel 32 of macerator 26. When the switch 16 is turned off, the on/off valve 30c disposed along supply line 30a is automatically turned off.

When the switch 16 has been turned on, waste material may be inserted into the waste inlet 23 for processing or aspirated through suction line 24. The waste material received through inlet 23 or by aspiration is reduced to a sludge or slurry form by the cutting action of the macerator 26 and mixing with water supplied from line 37c. The comminuted waste material, now in a slurry form, moves by way of gravity through conduit 39 from the macerator 26 into reservoir 27. The check valve 40 prevents the waste material from backflowing into the macerator once it has passed through the conduit 39 into the reservoir 27.

In another version of the invention, a waste shredder 48 is mounted over the waste inlet of the macerator 26 (see FIG. 6). The waste shredder includes a fixed cutter bar and rotating cutter arms which reduce the size of the infectious waste material by a cutting action to a physical size small enough to fit through the channel 32 of the macerator, thus allowing larger materials to be processed.

When the waste material has entered the reservoir 27 to the point where the level indicator 45 senses that the reservoir has received a desired batch amount of waste material for treatment, control circuitry in control means 50 automatically shuts off the waste processor forward/off/reverse switch 16 which in turn shuts of the aspirator pump 37 and macerator 26, thus preventing any additional waste to enter the reservoir until the waste already present in the reservoir has been treated and discharged.

The chemical used for treatment of the infectious waste material is of a formula and concentration sufficient, upon contact, to reduce and eliminate the pathogenic agents present in the type of waste being treatment. The treatment chemical can be in tablet, pellet, liquid, or powdered form. Because treatment is of a precisely controlled batch size of waste material, the amount of chemical which is used for the treatment of each batch of infectious waste may be precisely controlled. The treatment chemical enters the apparatus by way of the waste inlet 23.

In the preferred method, the chemical disinfectant used is a chlorine based compound in tablet form. Because the apparatus is suited for use with a disinfectant in solid tablet form, problems associated with long term storage and transport of disinfectants and splashing and aeration of the chemical during handling is minimized or eliminated altogether. The chlorine tablets are structurally bonded in such a manner that they can be both mechanically broken down to a powder by the waste disposal system and completely dissolved to a liquid upon contact with water in the waste disposal system.

Once macerator 26 and aspirator pump 37 have been deactivated as a result of level indicator 45 sensing that reservoir 27 is full, the control means 50 activates recirculation pump 28 and a timer 49 and activates the 3-way valve 43 to route the output of pump 28 back to reservoir 27 through return line 44. The function of pump 28 is to thoroughly mix the infectious waste with the disinfectant chemical and keep it in continuous suspension during the treatment process. In the preferred version of the invention the pump 28 is an open face impeller pump. In a further version of the invention the pump 28 is a grinder pump which further physically reduces the size of the infectious waste at the same time that it is being recirculated through the grinder pump and reservoir.

The detention time of each batch of infectious waste being recirculated through the reservoir 27 and pump 28 is controlled by timer 49 which is set for a time sufficient for the chemical to come in contact and reduce and eliminate all of the pathogenic agents present in the infectious waste, resulting in a non-toxic and non-infectious liquid or liquid sludge residue.

When the desired detention time has been reached, timer 49 sends a signal to the control means 50 which causes control means 50 to activate 3-way valve 43 to close return line 44 and open discharge line 46. The batch of treated waste material, now rendered non-toxic and non-infectious, is released under pressure supplied by the pump 28 into a sanitary sewer or other suitable discharge source. When the reservoir 27 has been emptied, level indicator 45 sends a signal to control means 50 which then deactivates pump 28 and activates 3-way valve 43 to close discharge line 46 and reopen return line 44.

In a further version of the invention, a suitable filter media 51 (FIG. 6) is provided in communication with discharge line 46. The batch of treated liquid or liquid sludge, rendered non-toxic and non-infectious, is released under pressure from the recirculation pump 28 into filter media 51 which removes the solid particulate matter component from the liquid or liquid residue. Any liquid remaining after the filtering process is released into a sanitary sewer, while the filter media and filtered waste is disposed of in a manner suitable for the disposal of solid waste.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus, adapted for use with a suitable disinfectant material, for treating and disposing of infectious waste material and converting it into a non-toxic and non-infectious waste residue, comprising:

a comminution means including an inlet opening for receiving infectious waste material and disinfectant material therethrough, said comminution means for reducing the particle size of the infectious waste material received through said inlet opening;

a reservoir in fluid communication with said comminution means and sized and arranged to receive the infectious waste material and disinfectant material from said comminution means in a slurry form;

a mixer means for mixing the slurry of infectious waste material and disinfectant material in said reservoir; and a control means for controlling the activating and deactivating of said mixer means, said control means including a level sensor operable to detect when the contents of said reservoir reaches a predetermined level corresponding to a desired batch size for treatment purposes, said control means operable to automatically activate said mixer means and deactivate said comminution means when the waste material in said reservoir reaches said predetermined level, said control means further including a timer which limits the operation of said mixer means to a desired control time sufficient to permit the disinfectant material in said reservoir to disinfect the infectious waste material in said batch.

2. The apparatus of claim 1 wherein said reservoir is an airtight enclosure and the apparatus further comprises conduit means communicating between said comminution means and said reservoir; and a one way check valve operably arranged and positioned along said conduit means to check the backflow of waste material and air from said reservoir, said mixer means including a pump located externally of said reservoir in fluid communication therewith, said pump being operable to mix the slurry in said reservoir by recirculating the slurry into the reservoir through said pump and into said comminution means while said mixer means is mixing a batch of waste material in said reservoir.

3. The apparatus of claim 1 wherein said comminution means includes a comminuting chamber and a channel positioned between said comminution means inlet opening and said comminuting chamber, said comminution means inlet opening positioned above said channel and opening upwardly, whereby infectious waste material received through said inlet opening is gravity fed through said channel into said comminuting chamber.

4. The apparatus of claim 1 and further comprising a waste discharge means for discharging the batch of waste material from said reservoir for disposal purposes, said timer controlling activation of said waste discharge means in correspondence with deactivation of said mixer means.

5. The apparatus of claim 1 wherein said comminution means has a water inlet and wherein the apparatus further comprises a water line conduit communicating with said comminution means water inlet, said control means further controlling the flow of water into said comminution means through said water line so as to allow water to enter said water inlet upon activation of said comminution means.

6. The apparatus of claim 1 wherein said mixer means includes a grinder pump associated with said reservoir and said mixer means, said grinder pump operable to further reduce the particle size of infectious waste material as said infectious waste material is being circulated through said mixer means and said reservoir.

7. The apparatus of claim 1 and further comprising a filter associated with said reservoir and said waste discharge means and operable therewith to filter particulate material from the treated slurry of infectious waste material discharged from said reservoir.

8. The apparatus of claim 1 wherein said channel is sized smaller than said comminution means inlet opening and the apparatus further comprises a waste shredder including a rotating cutter bar and grooved shredder ring associated with said comminution means inlet opening and operable to reduce the size of the infectious waste material sufficiently to permit the infectious waste material to be received through said inlet opening of said comminution means.

9. The apparatus of claim 1 and further comprising an aspiration means for aspirating waste material and water into said comminution means, said control means activating said comminution means upon activation of said aspiration means.

10. The apparatus of claim 2 and further comprising a filter associated with said reservoir and said waste discharge means and operable therewith to filter particulate material from the treated slurry of infectious waste material discharged from said reservoir.

11. The apparatus of claim 10 wherein said comminution means includes a comminuting chamber and a channel positioned between said comminution means inlet opening and said comminuting chamber, said comminution means inlet opening positioned above said channel and opening upwardly, whereby infectious waste material received through said inlet opening is gravity fed through said channel into said comminuting chamber.

12. The apparatus of claim 11 wherein said comminution means having a water inlet and wherein the apparatus further comprises a water line communicating with said comminution means water inlet, said control means further controlling the flow of water into said comminution means through said water line so as to allow water to enter said water inlet upon activation of said comminution means.

13. The apparatus of claim 12 wherein said mixer means includes a grinder pump associated with said reservoir and said mixer means, said grinder pump operable to further reduce the particle size of infectious waste material as said infectious waster material is being circulated through said mixer means and said reservoir.

14. The apparatus of claim 3 wherein said channel is sized smaller than said comminution means inlet opening and the apparatus further comprises a waste shredder including a rotating cutter bar and grooved shredder ring associated with said comminution means inlet opening and operable to reduce the size of the infectious waste material sufficiently to permit the infectious waste material to be received through said inlet opening of said comminution means.

15. The apparatus of claim 14 and further comprising an aspiration means for aspirating waste material and water into said comminution means, said control means activating said comminution means upon activation of said aspiration means.

16. The apparatus of claim 13 wherein said comminution means is a macerator.

17. The apparatus of claim 13 wherein said comminution means is a grinder pump.

18. The apparatus of claim 13 and further comprising a stainless steel housing enclosing said comminution means and said reservoir.

19. The apparatus of claim 13 wherein said control means includes an indicator light for indicating when said waste discharge means is activated by said timer.

20. The apparatus of claim 13 wherein said mixer means is an open face impeller pump.

21. The apparatus of claim 13 wherein said waste discharge means further includes a waste discharge line in communication with said reservoir and an air ventilation line communicating between said reservoir and said waste discharge means.

* * * * *

UNITED STATES PATENT AND TRADEMARK OFFICE
CERTIFICATE OF CORRECTION

PATENT NO. : 5,087,420

DATED : February 11, 1992

INVENTOR(S) : Edward E. Jackson

It is certified that error appears in the above-identified patent and that said Letters Patent is hereby corrected as shown below:

In Column 2 at Line 28, "in to" should read --into--

In Column 3 at Line 29, "A" should read --At--

In Column 3 at Line 40, "comminuted" should read --comminutes--

In Column 3 at Line 41, "time" should read --line--

In Column 5 at Line 46, "of" should read --off--

Signed and Sealed this

Twenty-second Day of June, 1993

Attest:

MICHAEL K. KIRK

*Attesting Officer*      *Acting Commissioner of Patents and Trademarks*